US006926728B2

(12) United States Patent
Zucherman et al.

(10) Patent No.: US 6,926,728 B2
(45) Date of Patent: Aug. 9, 2005

(54) CURVED DILATOR AND METHOD

(75) Inventors: James F. Zucherman, San Francisco, CA (US); Ken Y. Hsu, San Francisco, CA (US); Charles J. Winslow, Walnut Creek, CA (US); John Flynn, Concord, CA (US)

(73) Assignee: St. Francis Medical Technologies, Inc., Alameda, CA (US)

( * ) Notice: Subject to any disclaimer, the term of this patent is extended or adjusted under 35 U.S.C. 154(b) by 69 days.

(21) Appl. No.: 09/978,386

(22) Filed: Oct. 16, 2001

(65) Prior Publication Data

US 2003/0018350 A1 Jan. 23, 2003

Related U.S. Application Data

(60) Provisional application No. 60/306,289, filed on Jul. 18, 2001.

(51) Int. Cl.[7] ............................ A61B 17/00; A61B 17/56
(52) U.S. Cl. ............................ 606/190; 606/61; 606/53; 606/191
(58) Field of Search ............................ 606/61, 90, 191, 606/190; 623/17.11–17.16; 600/184

(56) References Cited

U.S. PATENT DOCUMENTS

| 592,579 | A | * | 10/1897 | Balkam ..................... 261/73 |
|---|---|---|---|---|
| 2,677,369 | A | | 5/1954 | Knowles |
| 3,426,364 | A | | 2/1969 | Lumb |
| 3,648,691 | A | | 3/1972 | Lumb et al. |
| 3,867,728 | A | | 2/1975 | Stubstad et al. |
| 3,875,595 | A | | 4/1975 | Froning |
| 4,309,777 | A | | 1/1982 | Patil |
| 4,349,921 | A | | 9/1982 | Kuntz |
| 4,369,769 | A | | 1/1983 | Edwards |
| 4,401,112 | A | | 8/1983 | Rezaian |
| 4,479,491 | A | | 10/1984 | Martin |

(Continued)

FOREIGN PATENT DOCUMENTS

| WO | WO 98/48717 | 11/1998 |
|---|---|---|
| WO | WO 99/26562 | 6/1999 |
| WO | WO 99/40866 | 8/1999 |
| WO | WO 99/42051 | 8/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 01/28442 A1 | 4/2001 |

OTHER PUBLICATIONS

Minns, R.J., et al., *Preliminary Design and Experimental Studies of a Novel Soft Implant for Correcting Sagittal Plane Instability in the Lumbar Spine*, SPINE vol. 22, No. 16, pp. 1819–1825, © 1997, Lippincott–Raven Publishers Waldemar Link, brochure entitled *Wirbelsäulen–Chirurgie: Instrumentarium Und Implantate Zur Wirbelsäulen–Chirurgie* (Spinal Surgery: Instrumentation and Implants for Spinal Surgery), Waldermar Link, Hamburg, Germany.

Haruo Tsuji, et al., *Ceramic Interspinous Block (CISB) Assisted anterior Interbody Fusion*, Journal of Spinal Disorders, vol.3, No.1, pp. 77–86, ©1990 Raven Press, Ltd., New York.

Richard W. Porter, MD, FRCS, FRCSE, *Spinal Stenosis and Neurogenic Claudication*, SPINE vol. 21, No. 17, pp. 2046–2052, ©1996, Lippincott–Raven Publishers.

*Primary Examiner*—Vy Bui
(74) *Attorney, Agent, or Firm*—Fliesler Meyer LLP

(57) ABSTRACT

The present invention generally relates to a dilator with a curved tip. The curved tip is machined through a specific range of diameters so that a physician can establish the diameter of the opening with the dilator inserted. The angle of the dilator also allows the physician to access the interspinous ligament through a minimally invasive opening in the patients back, minimizing the trauma caused to surrounding body tissue.

10 Claims, 4 Drawing Sheets

U.S. PATENT DOCUMENTS

| | | | |
|---|---|---|---|
| 4,501,269 A | 2/1985 | Bagby | |
| 4,553,273 A | 11/1985 | Wu | |
| 4,554,914 A | 11/1985 | Kapp et al. | |
| 4,599,084 A | 7/1986 | Nashef | |
| 4,599,086 A | 7/1986 | Doty | |
| 4,604,995 A | 8/1986 | Stephens et al. | |
| 4,611,582 A | 9/1986 | Duff | |
| 4,636,217 A | 1/1987 | Ogilvie et al. | |
| 4,643,178 A | 2/1987 | Nastari et al. | |
| 4,657,550 A | 4/1987 | Daher | |
| 4,685,447 A | 8/1987 | Iversen et al. | |
| 4,696,290 A | 9/1987 | Steffee | |
| 4,714,469 A | 12/1987 | Kenna | |
| 4,743,256 A | 5/1988 | Brantigan | |
| 4,772,287 A | 9/1988 | Ray et al. | |
| 4,790,303 A | 12/1988 | Steffee | |
| 4,834,757 A | 5/1989 | Brantigan | |
| 4,878,915 A | 11/1989 | Brantigan | |
| 4,904,260 A | 2/1990 | Ray et al. | |
| 4,904,261 A | 2/1990 | Dove et al. | |
| 4,913,134 A | 4/1990 | Luque | |
| 4,932,975 A | 6/1990 | Main et al. | |
| 4,936,848 A | 6/1990 | Bagby | |
| 4,946,378 A | 8/1990 | Hirayama et al. | |
| 4,961,740 A | 10/1990 | Ray et al. | |
| 4,969,888 A | 11/1990 | Scholten et al. | |
| 5,011,484 A | 4/1991 | Breard | |
| 5,015,247 A | 5/1991 | Michelson | |
| 5,026,373 A | 6/1991 | Ray et al. | |
| 5,035,716 A | 7/1991 | Downey | |
| 5,047,055 A | 9/1991 | Bao et al. | |
| 5,055,104 A | 10/1991 | Ray | |
| 5,059,193 A | 10/1991 | Kuslich | |
| 5,059,194 A | 10/1991 | Michelson | |
| 5,084,049 A | 1/1992 | Asher et al. | |
| 5,092,866 A | 3/1992 | Breard et al. | |
| 5,123,926 A | 6/1992 | Pisharodi | |
| 5,167,662 A | 12/1992 | Hayes et al. | |
| 5,180,381 A | 1/1993 | Aust et al. | |
| 5,192,327 A | 3/1993 | Brantigan | |
| 5,258,031 A | 11/1993 | Salib et al. | |
| 5,263,953 A | 11/1993 | Bagby | |
| 5,290,312 A | 3/1994 | Kojimoto et al. | |
| 5,304,178 A | 4/1994 | Stahurski | |
| 5,306,309 A | 4/1994 | Wagner et al. | |
| 5,334,194 A * | 8/1994 | Mikhail | 606/88 |
| 5,352,225 A | 10/1994 | Yuan et al. | |
| 5,361,766 A * | 11/1994 | Nichols et al. | 600/431 |
| 5,387,213 A | 2/1995 | Breard et al. | |
| 5,390,683 A | 2/1995 | Pisharodi | |
| 5,395,372 A | 3/1995 | Holt et al. | |
| 5,415,661 A | 5/1995 | Holmes | |
| 5,443,514 A | 8/1995 | Steffee | |
| 5,458,638 A | 10/1995 | Kuslich et al. | |
| 5,458,641 A | 10/1995 | Ramirez Jimenez | |
| 5,458,643 A | 10/1995 | Oka et al. | |
| 5,470,333 A | 11/1995 | Ray | |
| 5,496,318 A | 3/1996 | Howland et al. | |
| 5,505,732 A | 4/1996 | Michelson | |
| 5,514,180 A | 5/1996 | Heggeness et al. | |
| 5,534,028 A | 7/1996 | Bao et al. | |
| 5,534,029 A | 7/1996 | Shima | |
| 5,540,689 A | 7/1996 | Sanders et al. | |
| 5,549,679 A | 8/1996 | Kuslich | |
| 5,562,736 A | 10/1996 | Ray et al. | |
| 5,569,300 A * | 10/1996 | Redmon | 606/191 |
| 5,593,409 A | 1/1997 | Michelson | |
| 5,609,634 A | 3/1997 | Voydeville | |
| 5,645,597 A | 7/1997 | Krapiva | |
| 5,645,599 A | 7/1997 | Samani | |
| 5,653,761 A | 8/1997 | Pisharodi | |
| 5,674,295 A | 10/1997 | Ray et al. | |
| 5,674,296 A | 10/1997 | Bryan et al. | |
| 5,676,702 A | 10/1997 | Ratron | |
| 5,702,455 A | 12/1997 | Saggar | |
| 5,725,582 A | 3/1998 | Bevan et al. | |
| 5,766,252 A | 6/1998 | Henry et al. | |
| 5,824,098 A | 10/1998 | Stein | |
| 5,836,948 A * | 11/1998 | Zucherman et al. | 606/61 |
| 5,865,846 A | 2/1999 | Bryan et al. | |
| 5,885,299 A | 3/1999 | Winslow et al. | |
| 5,888,224 A | 3/1999 | Beckers et al. | |
| 5,888,226 A | 3/1999 | Rogozinski | |
| 5,891,147 A * | 4/1999 | Moskovitz et al. | 606/79 |
| 5,976,186 A | 11/1999 | Bao et al. | |
| 6,001,130 A | 12/1999 | Bryan et al. | |
| 6,022,376 A | 2/2000 | Assell et al. | |
| 6,113,639 A | 9/2000 | Ray et al. | |
| 6,156,067 A | 12/2000 | Bryan et al. | |
| 6,234,705 B1 | 5/2001 | Troxell | |
| 2001/0034535 A1 * | 10/2001 | Schultz | 606/190 |

* cited by examiner

CURVED DILATOR AND METHOD

RELATED CASES

This application claims priority to U.S. Provisional Patent Application entitled CURVED DILATOR AND METHOD, filed Jul. 18, 2001, Ser. No. 60/306,289 which is incorporated herein by reference.

FIELD OF THE INVENTION

The present invention generally relates to an instrument for dilating body tissue. More specifically, the present invention relates to an instrument that dilates the interspinous ligament which allows for precise initial placement of a trial sizing instrument or of an actual implant.

BACKGROUND OF THE INVENTION

Typically, a physician will use a dilating tool to create and dilate an opening in tissue. Such a tool, however, may not be configured to be conveniently positioned relative to the surgical site.

SUMMARY OF THE INVENTION

An embodiment of the present invention is a device for creating and dilating a hole in, for example, the interspinous ligament. The curved tip of the device has a range of dimensions so that a physician can also establish the diameter of the hole with the same device.

DETAILED DESCRIPTION OF THE INVENTION

Figure 1:
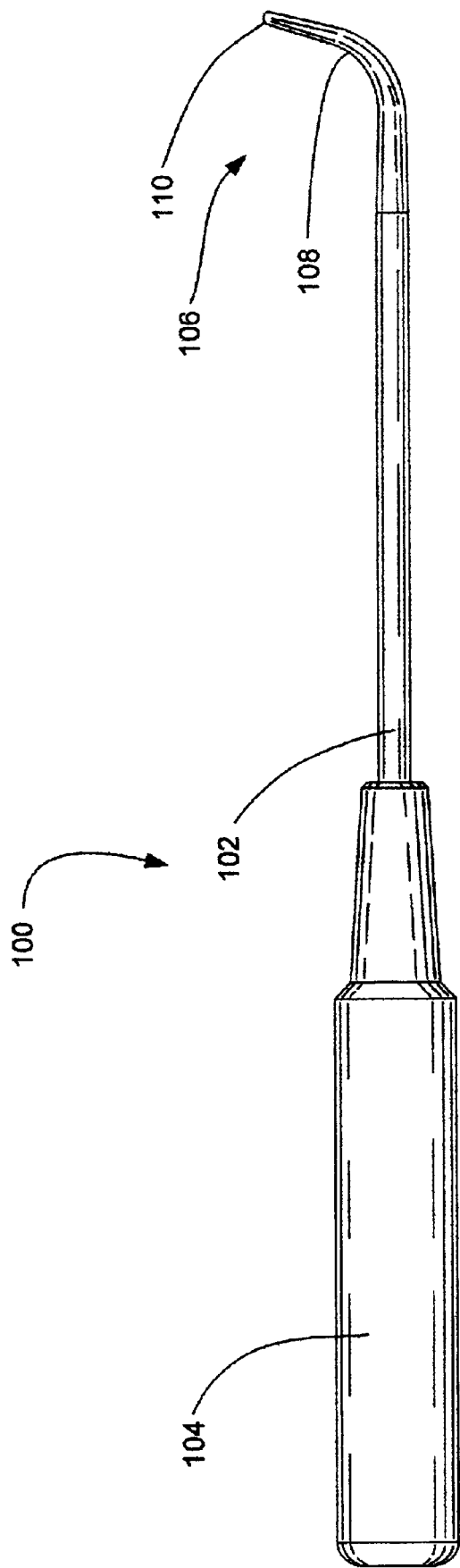
FIG. 1 is a perspective view of an embodiment of the present invention.

The device or curved dilator 100 creates and step or gradually dilates an opening in body tissue. In the preferred embodiment, the device 100 creates and step dilates an opening in the interspinous ligament. Referring to FIG. 1, the device 100 has an elongated body 102, a handle 104 and a tapered curved tip 106. The elongated body 102, including the tapered curved tip 106, is manufactured out of material such as, but not limited to, titanium-6A-4VEL 1 alloy which conforms to ASTM Standard F136-96: Standard Specification Wrought Titanium 6 Aluminum 4 Vanadium ELI (Extra Low Interstitial) Alloy (R56401) for surgical implant applications.

Implants are inserted between adjacent spinous processes to distract the spine segments and maintain them in a slightly flexed position to relieve symptoms of lumbar spinal stenosis and other conditions that cause pain which is associated with the back. Such implants have a spacer which remains in place between the adjacent spinous processes. The diameter of the spacer can vary to accommodate each patient.

An opening must be created in the interspinous ligament so that the implant can be inserted. The device 100 is used to step or gradually dilate the interspinous ligament and to confirm the correct implant size prior to its insertion. The curved tip 106 has a gradual taper with a first end 110 and a second end 108. The diameter of the tapered curved tip 106 gradually increases from the first end 110 to the second end 108. The diameter at the first end 110 and the second end 108 are preferably precisely machined to a known measurement. The device 100 can be marked so that the physician knows the range of diameters to which the device 100 was machined. For example, the handle 104 may be color coded, whereby a specific color correlates to a range of diameters or the largest diameter for a device 100. The color coding on the handle 104 helps the physician quickly distinguish the difference between the various devices 100.

Figure 2:
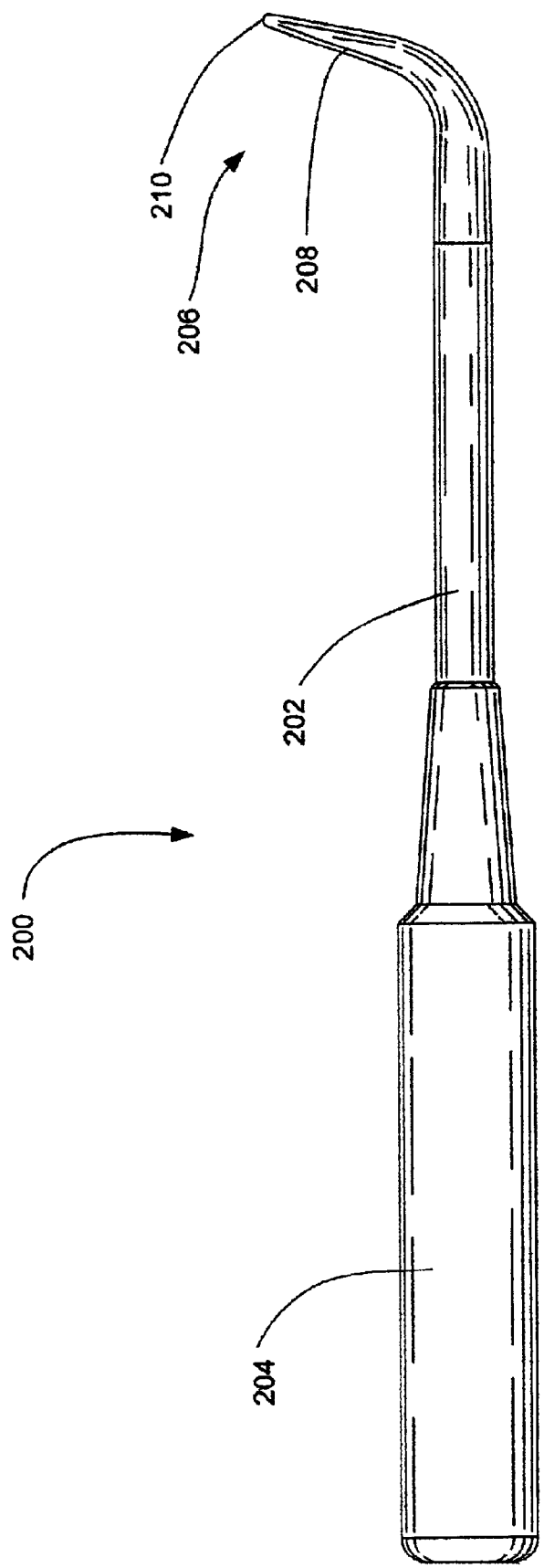
FIG. 2 is a perspective view of another embodiment of the present invention.
Figure 3:
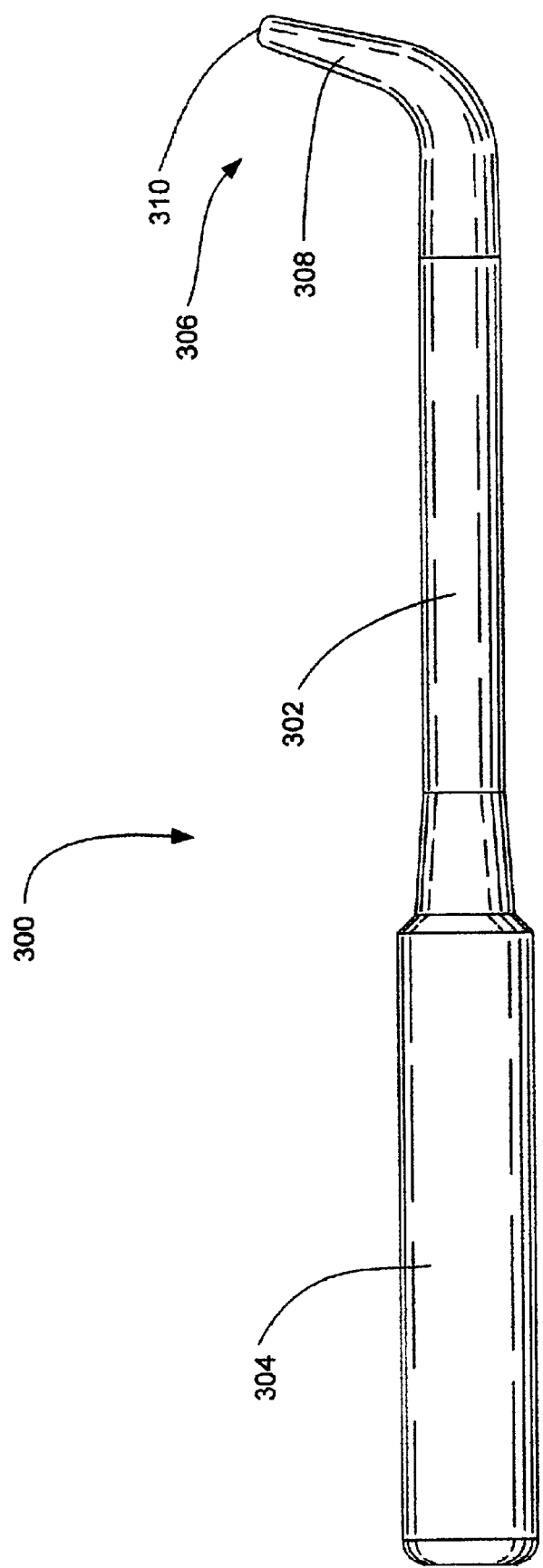
FIG. 3 is a perspective view of yet another embodiment of the present invention.
Figure 4:
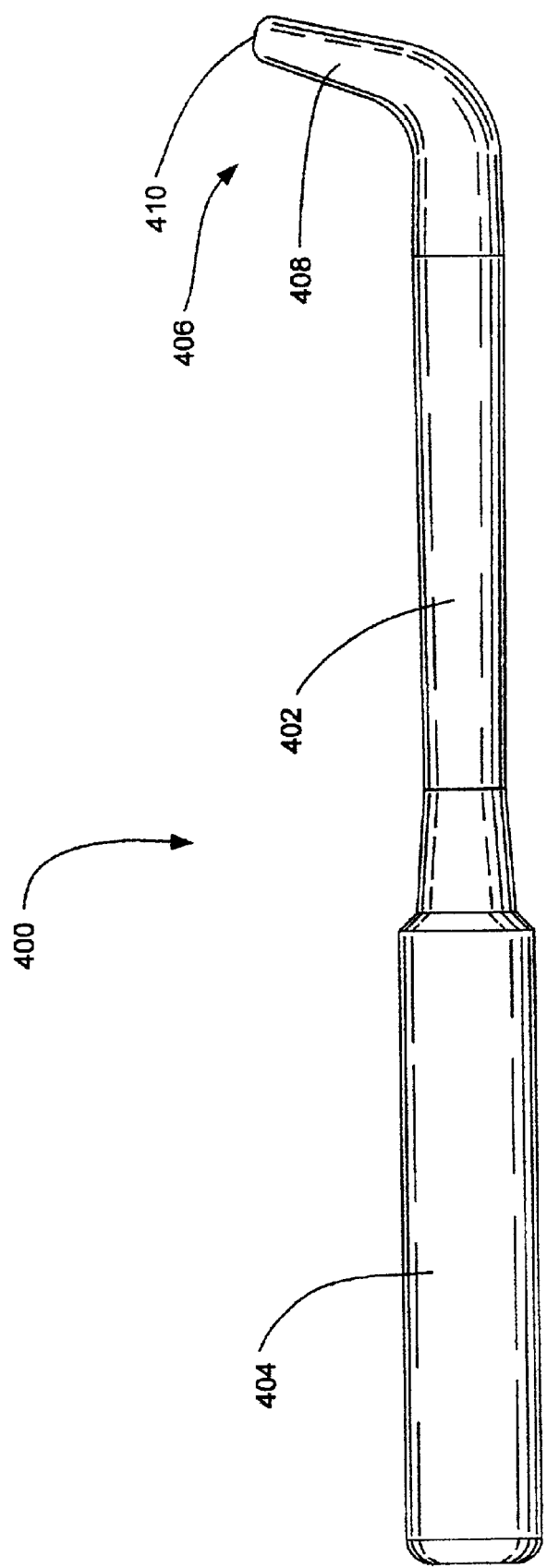
FIG. 4 is a perspective view of yet another embodiment of the present invention.

A physician may have several of the devices 100, 200, 300, 400 (see FIGS. 1–4) so that he or she may create and further dilate an opening. For example, a first device 100 may have a tapered curved tip 106 where the first end 110 has a diameter of one millimeter and the second end 108 has a diameter of three millimeters. The second device 200 may have a first end 210 with a diameter of three millimeters and a second end 208 having a diameter of six millimeters (see FIG. 2). The third device 300 may have a first end 310 with a diameter of six millimeters and a second end 308 having a diameter of nine millimeters (see FIG. 3). The fourth device 400 may have a first end 410 with a diameter of nine millimeters and the second end 408 having a diameter of twelve millimeters (see FIG. 4). One of obvious skill in the art will appreciate that these examples do not limit the possible ranges of diameters of the tapered curved tip 106, 206, 306, 406. Even though several different dilators may be used, the rest of the application will refer to the device 100 as illustrated in FIG. 1.

A physician can insert the first end 110 of first device 100 into the interspinous ligament to create an opening. By urging the curved tip 106 further into the interspinous ligament, up to the second end 108, the opening is dilated to three millimeters. Generally, an implant device has a spacer with a diameter larger than three millimeters, and thus the physician will remove the first device 100 from the opening and select a second device 200. As the opening is at three millimeters, the physician should select a second device 200 where the first end 210 has a diameter of three millimeters and a second end 208 having a diameter of six millimeters. By inserting the second device to the opening, the larger diameter curved tip 206 will further dilate the opening. This process should continue until the diameter of the opening is substantially the same as the diameter of the device to be implanted within the patient. The diameter of the opening is the diameter of the curved tip 206.

The device 100 can approach the interspinous ligament from one direction, through an incision. The tapered curved tip 106 is easily inserted into the spinous ligament. Typically, to insert an implant, a small incision is made while the patient is lying on his or her side. The curved tip 106 allows the physician to access the interspinous ligament through the small incision. By inserting the elongated body 102 into the incision, the physician can manipulate the curved tip 106 with the handle 104 and create an opening in the interspinous ligament with the curved tip 106. Accessing the interspinous ligament through a single incision further minimizes damage to surrounding body tissue.

Accordingly, the invention of the device can be used for an inventive method of dilation. The method includes making an incision in the patient and inserting the curved tip 106 of the tool preferably perpendicular to the back in a direction from a posterior position to an anterior position. The tip 106 is then preferably inserted perpendicular until it comes into the region above the interspinous ligament that is to be dilated. At that point, the tip 106 is substantially parallel to the ligament that is to be dilated. The handle of the device 100 would then be rotated and/or pivoted as the tip 106 is then urged into the interspinous ligament up to the second end 108. The device 100 can then be removed. Should further dilation be required, subsequent devices 100 with larger curved tips can be used.

The foregoing description of preferred embodiments of the present invention has been provided for the purposes of illustration and description. It is not intended to be exhaustive or to limit the invention to the precise forms disclosed. Many modifications and variations will be apparent to practitioners skilled in the art. The embodiments were chosen and described in order to best explain the principles of the invention and its practical application, thereby enabling others skilled in the art to understand the invention with various embodiments and with various modifications as are suited to the particular use contemplated. It is intended that the scope of the invention be defined by the following claims and their equivalents. The aspects, features, and advantages of the invention are also demonstrated in the figures and the claims.

What is claimed is:

1. A system for creating and dilating an opening in an interspinous ligament, the system comprising:
    a series of dilators, each dilator including:
        an elongated body having a proximal end and a distal end;
        a handle portion connected with the proximal end for manipulating the elongated body, and
        a tapered curved tip at the distal end adapted for being urged into the interspinous ligament, the tapered curved tip having a rigid shape and increasing from a first diameter to a second diameter, and
    wherein the first diameter of the tapered curved tip for a first dilator is sized such that the first dilator is adapted to create the opening in the interspinous ligament; and
    wherein the first diameter of the tapered curved tip for a subsequent dilator is substantially the same as the second diameter of the tapered curved tip of a preceding dilator.

2. The system of claim 1, wherein the tapered curved tip is positioned at an angle relative to the elongated body, so that the interspinous ligament maybe accessed with minimal damage to surrounding body tissue.

3. The system of claim 1, wherein each dilator further includes a mark for indicating a range of diameters of the tapered curved tip.

4. The system of claim 3, wherein the mark is a color coded handle portion.

5. The system of claim 1, wherein at least one of the devices includes a plurality of marks for measuring a width of a dilated opening, thereby allowing an implant to be properly sized.

6. A system for creating and dilating an opening in an interspinous ligament, the system comprising:
    a series of devices, each device including:
        an elongated body having a first end and a second end;
        a handle connected with the first end for manipulating the elongated body; and
        a tapered tip at the second end positioned about an axis that forms an angle with an axis of the elongated body, the tapered tip having a rigid shape and a diameter about the tip axis that increases from a first diameter to a second diameter;
    wherein the first diameter of the tapered tip for a first device of the series of devices is sized such that the first device is adapted to create the opening in the interspinous ligament; and
    wherein the first diameter of the tapered tip for a subsequent device of the series of devices is substantially the same as the second diameter of the tapered tip of a preceding device.

7. The system of claim 6, wherein the angle formed between the tip axis and the elongated body axis is such that the interspinous ligament may be accessed with minimal damage to surrounding body tissue.

8. The system of claim 6, wherein each device further includes a mark for indicating a range of diameters of the tapered tip.

9. The system of claim 6, wherein the mark is a color coded handle.

10. The system of claim 6, wherein each device includes a plurality of marks for measuring a width of a dilated opening, thereby allowing an implant to be properly sized.

* * * * *